United States Patent [19]
Nason

[11] Patent Number: 5,869,003
[45] Date of Patent: Feb. 9, 1999

[54] SELF CONTAINED DIAGNOSTIC TEST UNIT

[76] Inventor: Frederic L. Nason, 941 Avenida Acaso, Camarillo, Calif. 93010

[21] Appl. No.: 60,840

[22] Filed: Apr. 15, 1998

[51] Int. Cl.⁶ .................................................... G01N 1/02
[52] U.S. Cl. .............................. 422/58; 422/61; 422/100; 422/102
[58] Field of Search ................................. 422/56, 58, 61, 422/99–102, 104

[56] References Cited

U.S. PATENT DOCUMENTS

| | | |
|---|---|---|
| D. 369,214 | 4/1996 | Nason . |
| 2,490,168 | 12/1949 | Strauss . |
| 2,510,490 | 6/1950 | Ager . |
| 3,004,681 | 10/1961 | Jinkens . |
| 3,163,160 | 12/1964 | Cohen . |
| 3,324,855 | 6/1967 | Heimlich . |
| 3,450,129 | 6/1969 | Avery et al. . |
| 3,495,917 | 2/1970 | Truhan . |
| 3,640,268 | 2/1972 | Davis . |
| 3,674,007 | 7/1972 | Freis . |
| 3,773,035 | 11/1973 | Arnoff . |
| 3,776,220 | 12/1973 | Monaghan . |
| 3,792,699 | 2/1974 | Tobin . |
| 3,883,396 | 5/1975 | Thomas, Jr. . |
| 3,890,204 | 6/1975 | Avery . |
| 3,890,954 | 6/1975 | Greenspan . |
| 3,913,564 | 10/1975 | Freshley . |
| 3,915,806 | 10/1975 | Horlach . |
| 3,918,435 | 11/1975 | Beall et al. . |
| 3,923,604 | 12/1975 | Monaghan . |
| 3,954,563 | 5/1976 | Mennen . |
| 3,958,571 | 5/1976 | Bennington . |
| 4,014,746 | 3/1977 | Greenspan . |
| 4,014,748 | 3/1977 | Spinner et al. . |
| 4,059,404 | 11/1977 | Schuster et al. . |
| 4,175,008 | 11/1979 | White . |
| 4,184,483 | 1/1980 | Greenspan . |
| 4,196,167 | 4/1980 | Olsen . |
| 4,223,093 | 9/1980 | Newman . |
| 4,300,910 | 11/1981 | Pannwitz . |
| 4,311,792 | 1/1982 | Avery . |
| 4,312,950 | 1/1982 | Snyder . |
| 4,340,670 | 7/1982 | Mennen . |
| 4,353,868 | 10/1982 | Joslin . |
| 4,355,113 | 10/1982 | Mennen . |
| 4,387,725 | 6/1983 | Mull . |
| 4,409,988 | 10/1983 | Greenspan . |
| 4,562,043 | 12/1985 | Mennen . |
| 4,586,604 | 5/1986 | Alter . |
| 4,635,488 | 1/1987 | Kremer . |
| 4,653,510 | 3/1987 | Koll . |
| 4,707,450 | 11/1987 | Nason . |
| 4,770,853 | 9/1988 | Bernstein . |
| 4,790,640 | 12/1988 | Nason . |
| 4,813,432 | 3/1989 | Saint-Amand . |
| 4,978,504 | 12/1990 | Nason . |
| 5,078,968 | 1/1992 | Nason . |
| 5,238,649 | 8/1993 | Nason . |
| 5,256,537 | 10/1993 | Phillips et al. ............................ 422/58 |
| 5,266,266 | 11/1993 | Nason . |
| 5,556,789 | 9/1996 | Goerlach-Graw et al. ............... 422/58 |

FOREIGN PATENT DOCUMENTS

| | | |
|---|---|---|
| 0058008 | 8/1982 | European Pat. Off. . |
| 0155747 | 9/1995 | European Pat. Off. . |

*Primary Examiner*—Lyle A. Alexander
*Attorney, Agent, or Firm*—Kelly Bauersfeld Lowry & Kelley, LLP

[57] ABSTRACT

A self contained diagnostic test unit is provided for use in the collection and analysis of a biological specimen or the like. The test unit comprises a tubular housing defining a specimen chamber for receiving a specimen disposed, for example, on a specimen collection device such as a swab or the like. A reagent dispenser cap may be associated with the housing for delivering one or more selected reagents to the specimen chamber for contacting the collected specimen. A diagnostic strip assembly is mounted on the housing and comprises a diagnostic test strip adapted for controlled contact with the collected specimen, for causing a portion of the specimen to flow by wick action through the test strip. The specimen interacts with one or more reagents disposed along the test strip to produce a visible reaction such as a color change which can be observed from the exterior of the test unit to provide an indication of the result of a selected diagnostic test.

30 Claims, 7 Drawing Sheets

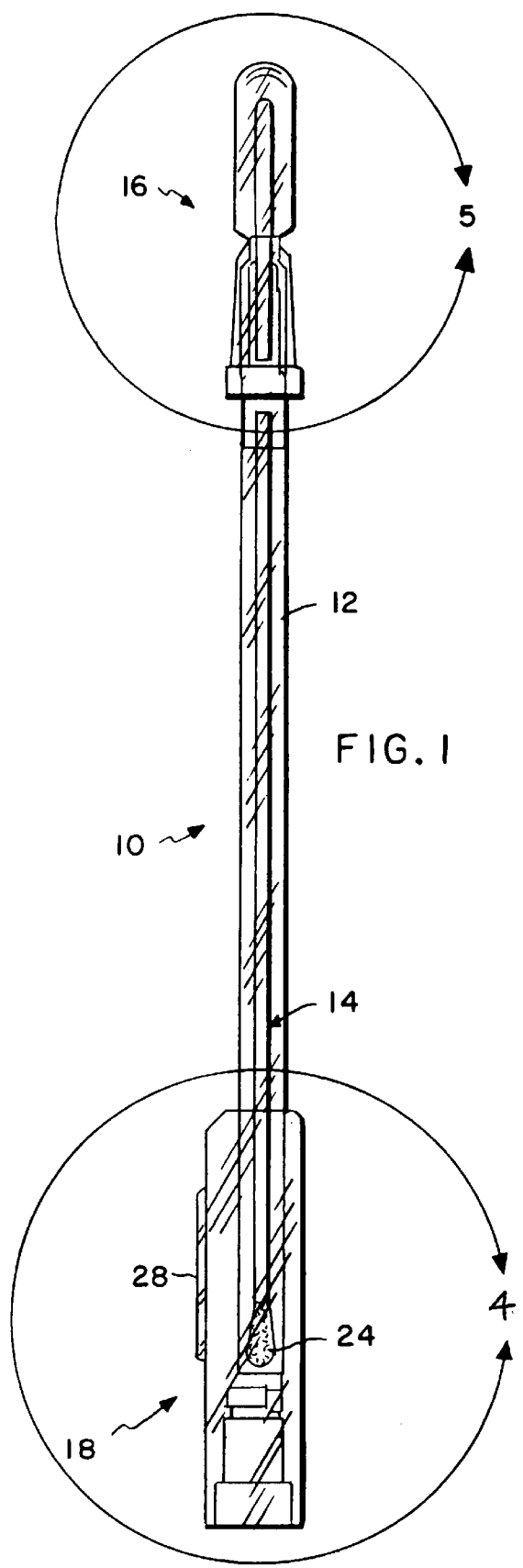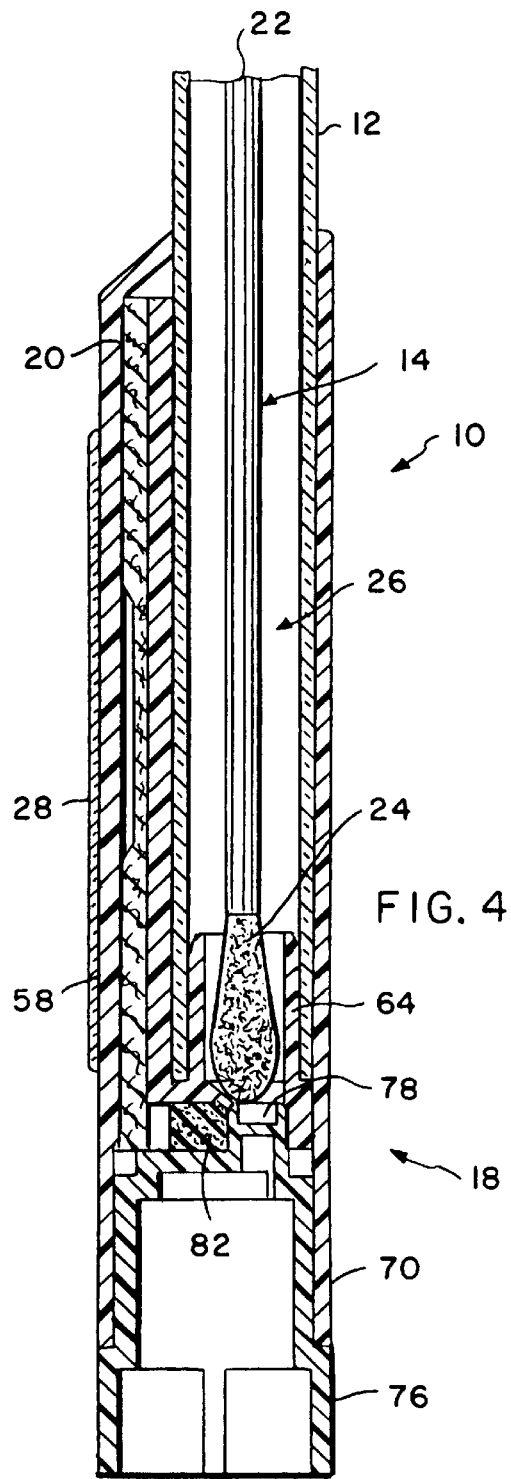

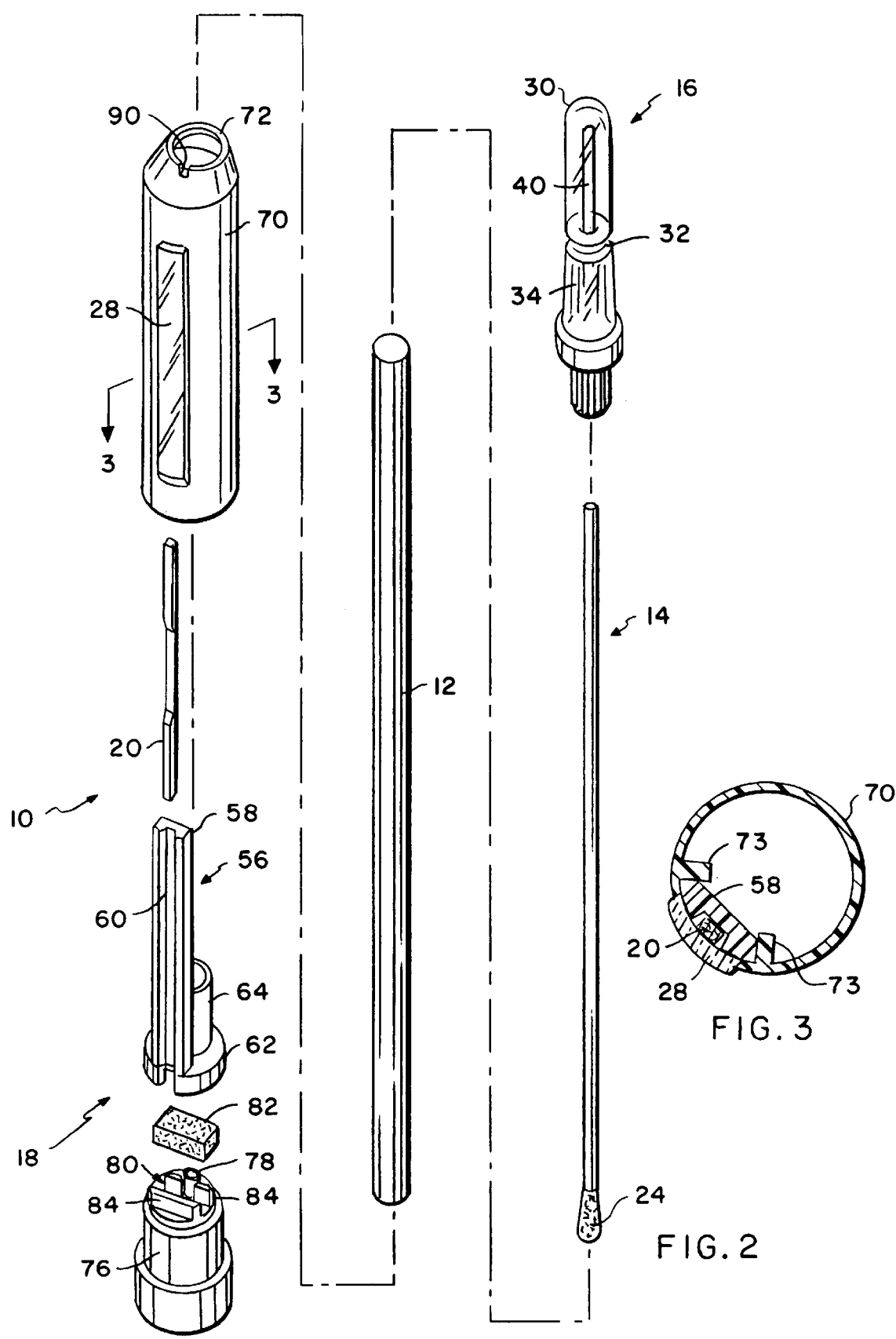

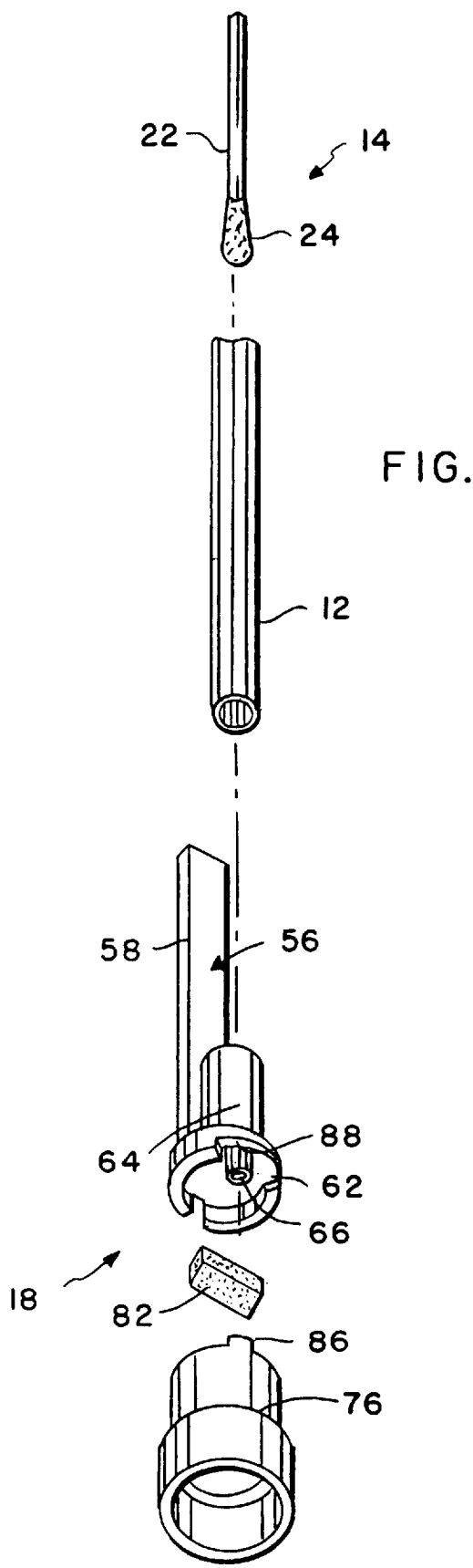
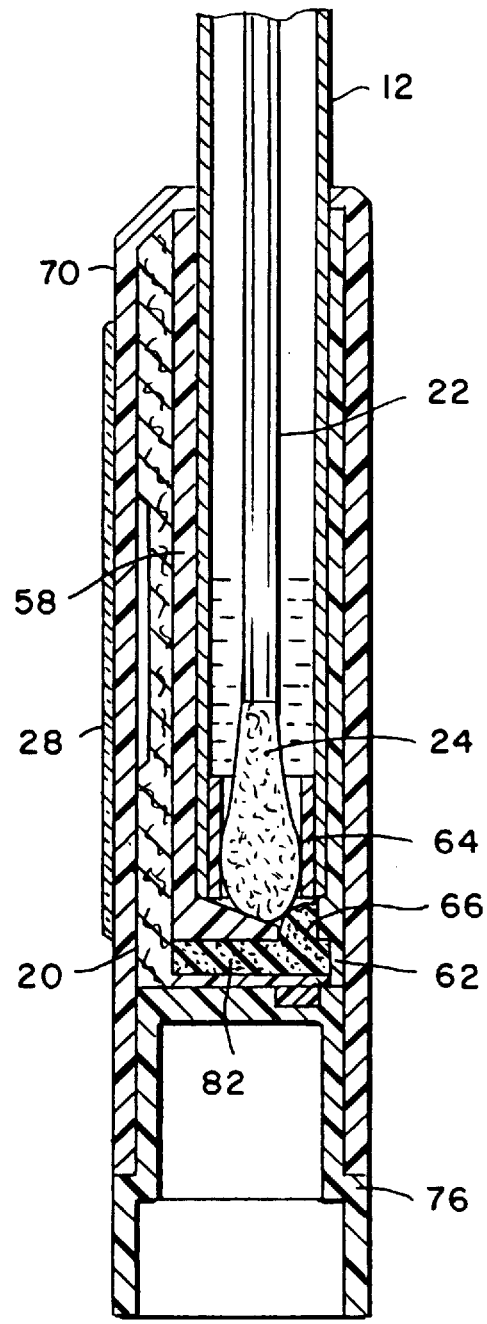
FIG. 11
FIG. 12

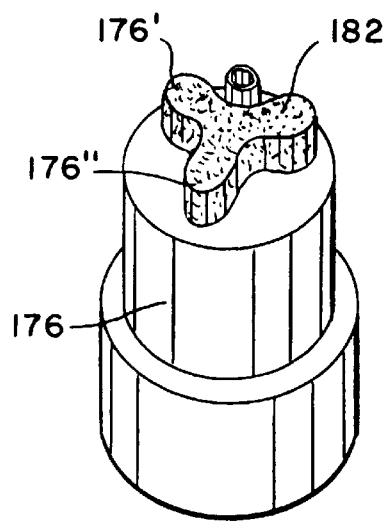
FIG. 13
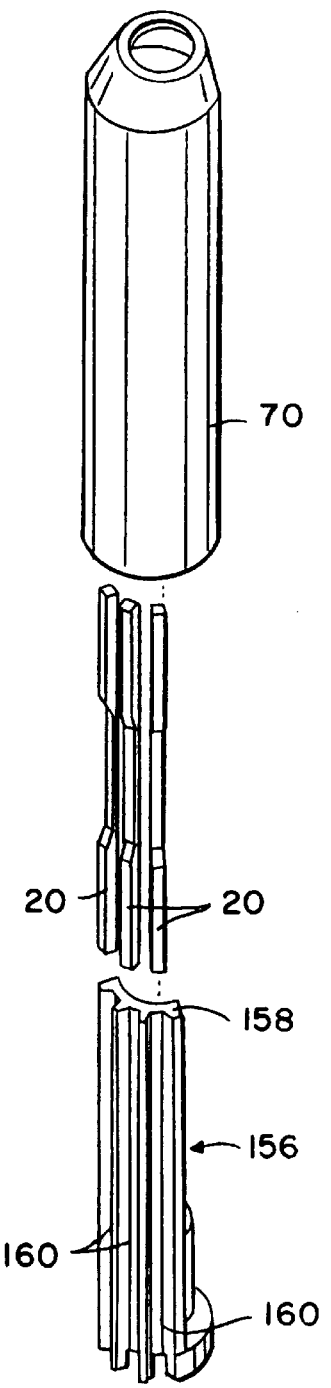
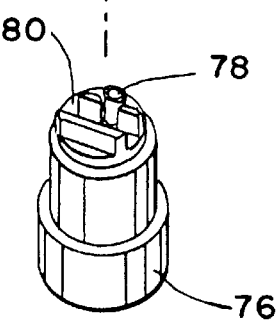
FIG. 14

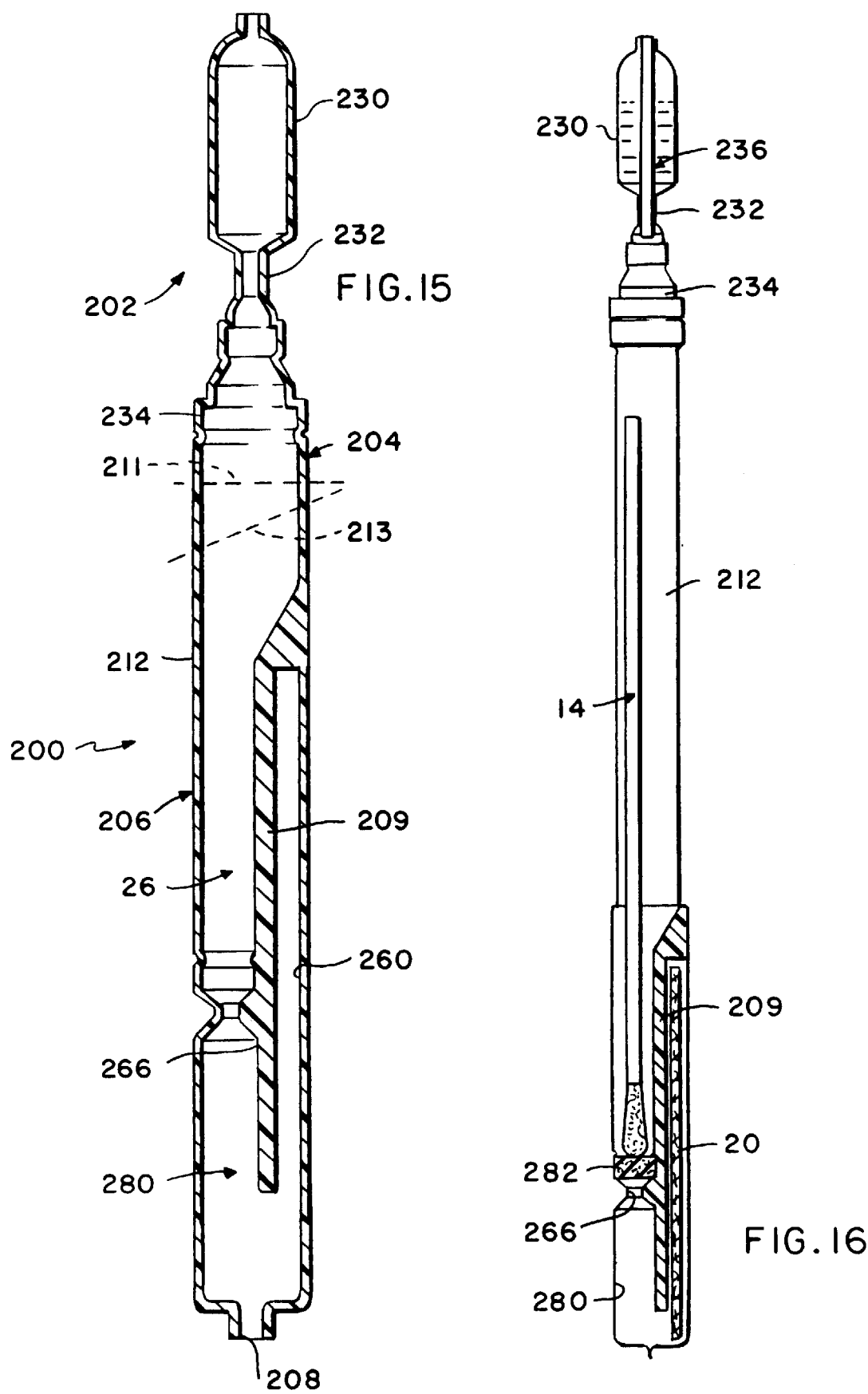

SELF CONTAINED DIAGNOSTIC TEST UNIT

BACKGROUND OF THE INVENTION

This invention relates generally to improvements in devices and kits used for collecting and analyzing biological specimens, particularly such as medical specimens. More specifically, this invention relates to an improved and substantially self contained test unit or kit for collecting and analyzing a biological specimen.

Medical swabs are generally known in the art for use in collecting biological specimens from a patient for further analysis. Such medical swabs commonly comprises a fibrous swab tip at one end of an elongated stick or shaft which is manually handled to contact the swab tip with selected tissue cells or other biological specimen obtained, for example, within the ear, nose or throat of a patient. As a result, some of the targeted biological specimen adheres to the swab tip which then can be contacted with one or more chemical reagents to indicate the presence of infection or other information regarding patient condition. Tests commonly performed with such patient specimens include, by way of example, fluorescent tests, enzymatic tests, monoclonal based tests, agglutination tests, and others. Moreover, swabs and similar reagent test methods are also used in a variety of nonmedical applications to determine the presence of selected biological organisms on a selected surface, such as a food preparation surface in a restaurant or the like.

In accordance with standard specimen collection and test preparation techniques, the biological specimen is normally transferred from the swab tip to a slide or other laboratory apparatus such as a test tube or the like for contact with the selected reagent or reagents and further analysis. However, it is frequently difficult to ensure transfer of a sufficient specimen quantity from the swab tip to the laboratory slide or test tube to ensure accurate test results. Moreover, in many instances, the collected specimen must be transported to an off-site laboratory for performance of selected assays, but delays between the time of specimen collection and actual test performance can result in partial or complete drying of the specimen, with a corresponding decrease in test reliability.

In addition, such conventional handling of a biological specimen in the course of preparing and/or performing an analysis undesirably exposes personnel to direct contact with the collected organism, wherein direct contact with infectious or toxic organisms can be especially undesirable. In this regard, a variety of swab-type specimen collection and test devices have been proposed in efforts to provide enhanced contact between a specimen and reagents, or to sustain the specimen in an improved manner during transport to a laboratory, while at the same time reducing or minimizing risk of direct personnel contact with the collected specimen. See, for example, the test units or kits disclosed in U.S. Pat. Nos. 3,792,699; 4,707,450; 4,978,504; 5,078,968; 5,238,649; and 5,266,266, wherein a collected specimen on a swab or the like is placed into a specimen chamber formed within a compact housing which includes means for delivering one or more chemical reagents for contacting the specimen on the swab. In some test procedures, the mixed specimen and reagent is adapted for delivery from the specimen chamber to external components such as a laboratory slide, or to additional chambers within the test unit for contacting the specimen with additional reagents which may be provided in liquid or dry form. U.S. Pat. No. 5,238,649 discloses test unit variations including an elongated diagnostic strip adapted for wick flow passage of the mixed specimen and reagent, and wherein the diagnostic strip may impregnated with one or more additional reagents selected to provide a visual indicator of test result.

The present invention pertains to an improved specimen test unit or kit of the type including a diagnostic strip for providing a visual indicator of test result, wherein the diagnostic strip is assembled with the test unit in a compact and convenient package which is substantially fully self contained, relatively simple to manufacture, and relatively easy to use while providing test results which are highly reliable and easy to read.

SUMMARY OF THE INVENTION

In accordance with the invention, a substantially self contained diagnostic test unit is provided for collecting and analyzing a biological specimen. The test unit comprises a tubular housing defining a specimen chamber for receiving a biological specimen collected, for example, on a swab or the like. A reagent dispenser cap is removably mounted on the housing to permit placement of the specimen into the specimen chamber, at which time the dispenser cap can be manipulated to deliver one or more selected chemical reagents to the specimen chamber for contacting the collected specimen. A diagnostic strip assembly is also mounted on the housing and includes a diagnostic strip extending along the housing, substantially in parallel relation to the specimen chamber. Transfer means are provided for transferring mixed specimen and reagent from the specimen chamber for contacting one end of the diagnostic strip and for wick flow therethrough into contact with one or more additional reagents selected to yield a visual test result.

In the preferred form, the reagent dispenser cap is removably mounted on an upper or proximal end of the tubular housing and cooperates therewith to define the specimen chamber into which a swab or the like bearing the collected specimen can be placed. The dispenser cap is desirably constructed according to U.S. Pat. No. 5,266,266, which is incorporated by reference herein, and can be manipulated to deliver one or more reagents to the specimen chamber for contacting the collected specimen.

The diagnostic strip assembly is mounted onto the tubular housing at a lower or distal end thereof. This strip assembly comprises a strip holder for supporting an elongated porous diagnostic strip to extend generally longitudinally along the tubular housing, with a lower end of the diagnostic strip disposed generally at the housing lower end. A protective outer sleeve is carried about the strip holder and strip, and includes a transparent window through which the diagnostic strip is externally visible. In a preferred form, the window is designed for magnified viewing of the diagnostic strip for improved visual perception of a test result indicated by the strip.

The transfer means of the diagnostic strip assembly comprises means forming a flow passage between the specimen chamber and the adjacent lower end of the diagnostic strip. In the preferred form, a transfer wick is mounted along this passage and may be impregnated with one or more additional reagents. Flow of mixed specimen and reagent from the specimen chamber to the transfer wick may be controlled by a valve member provided as part of the diagnostic strip assembly, wherein the valve member is movable to permit such flow when desired. Alternately, such flow can be regulated by impregnating or coating the transfer wick with agents designed for controlled time dissolution following the introduction of liquid reagent into the specimen chamber. In either case, the transfer wick can be mounted under compression within the transfer flow path, and adapted to expand sufficiently to extend into the lower end of the specimen chamber for directly contacting the tip of a swab placed into the specimen chamber.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a side elevational view illustrating one preferred construction for a self contained diagnostic test unit embodying the novel features of the invention;

FIG. 2 is an exploded perspective view depicting assembly of the components of the test unit shown in FIG. 1;

FIG. 3 is an enlarged transverse sectional view of a portion of the test unit, taken generally on the line 3—3 of FIG. 2;

FIG. 4 is an enlarged fragmented vertical sectional view of a lower portion of the test unit, corresponding generally with the encircled region 4 of FIG. 1, and showing a diagnostic strip assembly mounted onto a lower end of a tubular housing defining a specimen chamber.

FIG. 11 is an exploded perspective view of a lower portion of the test unit, illustrating further construction details of components forming the diagnostic strip assembly;

FIG. 12 is an enlarged fragmented vertical sectional view similar to FIG. 3, illustrating delivery of mixed specimen and reagent to a diagnostic strip for providing a visual indication of test result;

FIG. 13 is an exploded perspective view of a portion of the diagnostic strip assembly in one alternative preferred form;

FIG. 14 is an exploded perspective view showing the diagnostic strip assembly in a further alternative preferred form;

FIG. 15 is a side elevational view illustrating construction of the diagnostic test unit from a blow molded blank; and FIG. 16 is a side elevational view of the diagnostic test unit in an alternative preferred form, utilizing components of the blow molded blank of FIG. 15.

DETAILED DESCRIPTION OF THE PREFERRED EMBODIMENTS

Figure 5:
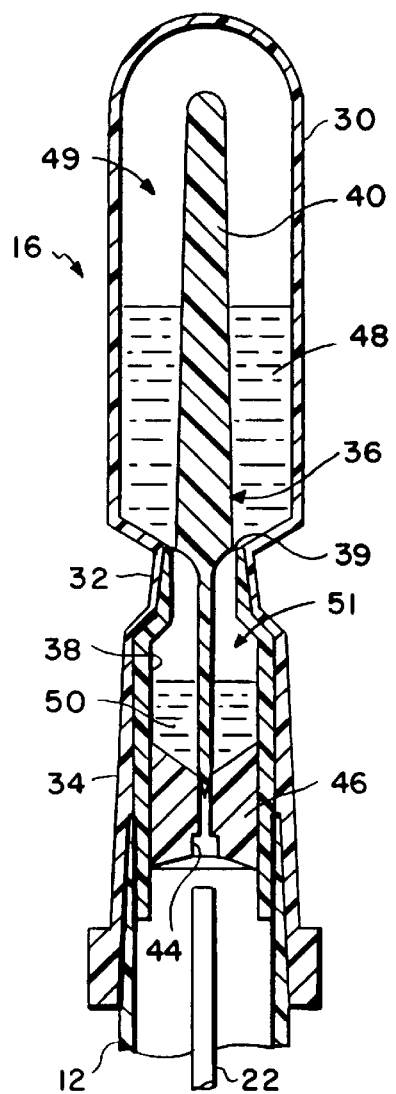
FIG. 5 is an enlarged fragmented vertical sectional view of an upper portion of the test unit, corresponding generally with the encircled region 5 of FIG. 1, and showing a reagent dispenser cap mounted onto an upper end of the tubular housing.

As shown in the exemplary drawings, an improved and substantially self contained diagnostic test unit referred to generally in FIGS. 1 and 2 by the reference numeral 10 is provided for collecting a biological specimen and for performing a selected test, such as a medical assay, with respect to the collected specimen. The diagnostic test unit comprises an elongated tubular housing 12 into which a collected specimen on a swab 14 or the like can be placed. A reagent dispenser cap 16 is removably mounted at one end of the tubular housing 12 and can be manipulated to deliver one or more selected chemical reagents for contacting the specimen. A diagnostic strip assembly 18 is mounted at an opposite end of the housing 12 and includes means for delivering mixed specimen and reagent to contact one end of an elongated diagnostic test strip 20. The mixed specimen and reagent flow along the test strip 20 by wick action, wherein the test strip 20 includes means for providing a direct visual indication of test result.

The diagnostic test unit 10 of the present invention provides a relatively simple, compact and cost-efficient device for facilitated collecting and substantially immediate on-site testing of biological specimens such as tissue, cells, body fluid, and the like obtained from a patient, or from another target source such as a food preparation surface in a restaurant or the like. The test unit 10 enables quick and easy specimen collection with the swab 14 or other suitable collection implement, followed by prompt placement of the collected specimen into the tubular housing 12 which is substantially closed and sealed to minimize risk of direct personnel contact with the collected organism. Thereafter, the reagent dispenser cap 16 and the diagnostic strip assembly 18 mounted on the tubular housing 12 can be manipulated in a sequence appropriate to the particular assay to analyze the collected specimen, including reagent contacting steps, time delay steps, etc. Importantly, the test unit 10 enables the collected specimen to be analyzed and presented in the appropriate form to the diagnostic strip 20 which is treated with one or more agents adapted to react with the specimen in a manner yielding a visible test result. This visible test result can be readily observed by the person performing the test, in a prompt manner and under test conditions conducive to highly reliable and consistent test results. After initial specimen collection, human contact with the specimen is thus substantially precluded throughout the test protocol, and the entire device with the collected specimen safely contained therein may be discarded as a unit when the test is concluded.

As shown in detail in FIGS. 1–12 with respect to one preferred form of the invention, the diagnostic test unit 10 constitutes an elongated and relatively thin implement having an overall size and shape for easy manual handling during use. The swab 14 is shown conventional in form, to include an elongated shaft or shank 22 having a swab tip or bud 24 of absorbent fibrous cotton material or the like at one end thereof. This swab construction will be recognized as generally standard in the medical arts and in other fields for use in collecting a biological specimen on the swab tip 24. It will be understood, however, that other swab constructions and other types of specimen collection implements may be used with the test unit 10 of the present invention.

The illustrative swab 14 is shaped for convenient and easy placement, following collection of a specimen on the tip 24 thereof, directly into the elongated hollow tubular housing 12 which can be economically formed from molded or blown plastic. The hollow interior of this housing 12 defines a specimen chamber 26 into which the collected specimen is placed, preferably by simply dropping the swab 14 directly into the specimen chamber 26. In this regard, a lower or distal end of the specimen chamber is closed by the diagnostic strip assembly 18 mounted on the housing 12, and an upper or proximal end of the housing is closed by the reagent dispenser cap 16 removably mounted onto the housing 12 in a manner permitting the swab 14 to be placed therein. As shown, for best test results, the swab 14 is placed into the specimen chamber 26 with the tip 24 positioned generally at the proximal end of the housing 12, in close association with the diagnostic strip assembly 18.

In general terms, the diagnostic strip assembly 18 includes means for supporting the elongated diagnostic strip 20 in a position lying or extending substantially alongside the specimen chamber 26 at the lower or proximal end of the tubular housing 12, with a lower end of the strip 20 positioned for controlled exposure to and contact with the specimen placed into the specimen chamber 26. More particularly, the strip assembly 18 includes transfer means for controlled or regulated delivery of the specimen, typically preconditioned and/or carried by one or more reagents in liquid form added to the specimen chamber 26 by manipulation of the reagent dispenser cap 16. Upon contacting the lower end of the diagnostic strip 20, the specimen flows upwardly therein by wick action. As the specimen wets the strip 20, the specimen also contacts and reacts with one or more reagents placed along the strip 20 to produce a visible reaction such as a color change indicative of test result. The visible reaction can be observed directly and immediately through a transparent window 28 forming a portion of the strip assembly 18 and positioned to overlie the diagnostic strip 20 or portions thereof sufficient to reveal the test result.

Figure 6:
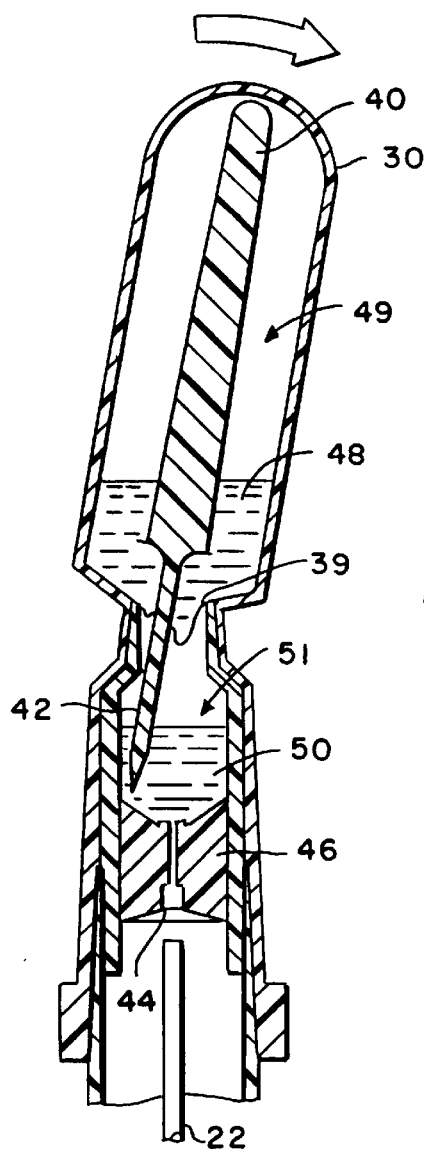
FIG. 6 is a fragmented sectional view similar to FIG. 5, depicting manipulation of the reagent dispenser cap for release of one or more reagents therein.
Figure 7:
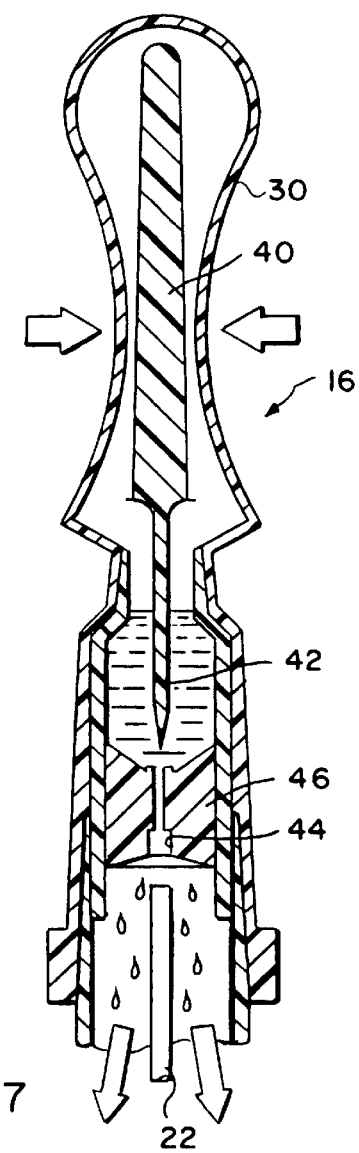
FIG. 7 is a fragmented sectional view similar to FIGS. 5 and 6, showing further manipulation of the reagent dispenser cap.

The reagent dispenser cap 16 is shown in detail in one preferred form in FIGS. 5–7, constructed in accordance with U.S. Pat. No. 5,266,266 and copending U.S. Ser. No. 08/829, 248, filed Mar. 31, 1997, which are incorporated by reference herein. As shown, the dispenser cap 16 comprises an outer shell or case of blown or molded plastic to include an upper deformable squeeze bulb 30 joined integrally by a narrowed neck 32 to a lower mounting sleeve 34. The squeeze bulb 30 is sufficiently transparent to permit viewing of an internal closure member in the form of a nib unit 36 of injection molded plastic or the like fitted therein, with a cylindrical liner 38 pressed into the lower mounting sleeve 34. This liner 38 has an upper end which transitions through the neck 32 and is joined integrally by a thin rupturable or frangible membrane ring 39 to a break-off nib 40 projecting upwardly into the interior of the squeeze bulb 30. A central stem pin 42 is provided as an extension of the nib 40 and projects downwardly from the nib 40 within the liner 38 to engage and sealingly close an outlet port 44 formed in a seal plug 46 pressed into the liner 38.

The reagent dispenser cap 16 is assembled in a manner to receive at least one and preferably two chemical reagents, shown in liquid form in FIGS. 5–7. More specifically, a first reagent 48 is placed into a first chamber 49 defined by the interior volume of the squeeze bulb 30, followed by press-fit installation of the nib unit 36 into the outer case so that the upper end of the liner 38 seals through the neck 32, in cooperative relation with the membrane 39 and associated nib 40. A second reagent 50 may then be placed into the interior of the liner 38, within a second chamber 51, followed by press-fit placement of the seal plug 46 in a position with the stem pin 42 closing the outlet port 44. The dispenser cap, thus assembled, defines a downwardly open annulus 52 for receiving and sealingly engaging with the upper end of the tubular housing 12 to provide a normally closed and sealed unit which can be appropriately sanitized.

When it is desired to perform a test, the reagent dispenser cap 16 is placed on the upper or proximal end of the housing 12 to enclose the swab 14 with specimen collected on the tip 24 thereof within the specimen chamber 26, as shown in FIG. 5. The reagent dispenser cap 16 is then manipulated to intermix the two reagents 48 and 50 by initially bending or deforming the squeeze bulb 30 through an angular stroke sufficient to cause bendover displacement of the nib 40 to rupture the membrane ring 39, as viewed in FIG. 6. This action breaks the seal between the two reagent chambers 49 and 51, to enable the two reagents to flow together and mix. Further bendover displacement of the squeeze bulb 30 will retract the stem pin 42 from the outlet port 44 (FIG. 6), whereupon the squeeze bulb 30 can be manually squeezed (FIG. 7) to express the mixed reagents 48, 50 through the outlet port 44 into the specimen chamber 26. With the test unit 10 held in an essentially upright orientation, the mixed reagents 48, 50 will drain to the lower end of the specimen chamber 26 to flood the swab tip 24 and the specimen collected thereon.

Figure 8:
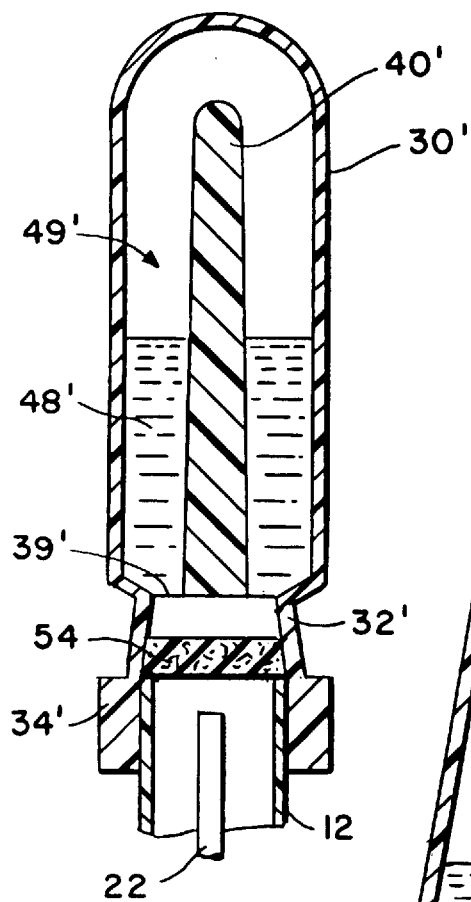
FIG. 8 is an enlarged fragmented vertical sectional view similar to FIG. 5, but illustrating an alternative preferred construction for the reagent dispenser cap.
Figure 9:
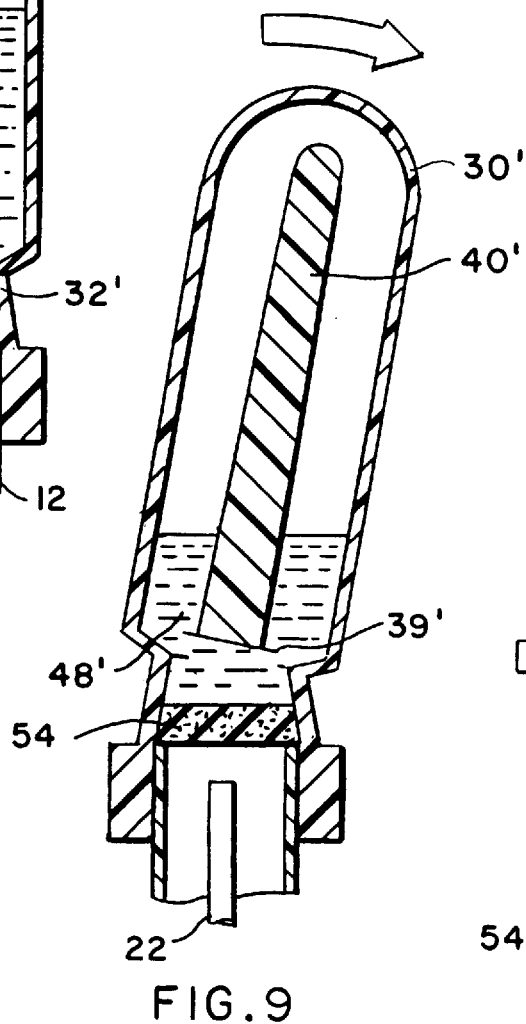
FIG. 9 is fragmented sectional view similar to FIG. 8, showing manipulation of the reagent dispenser cap of FIG. 8 for release of one or more reagents therein.
Figure 10:
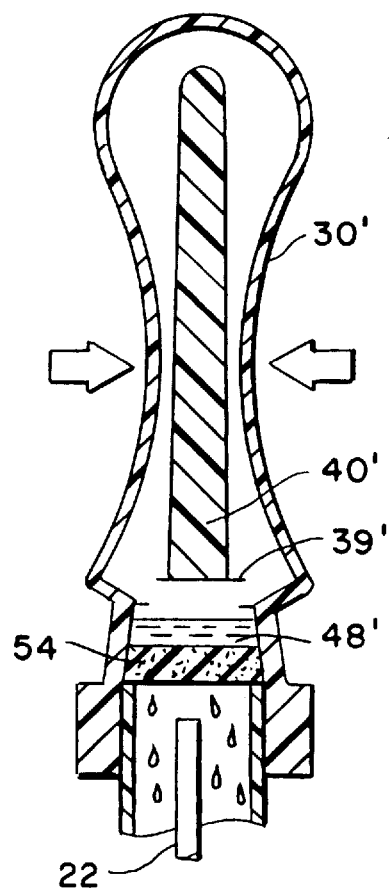
FIG. 10 is a fragmented sectional view similar to FIGS. 8 and 9, showing further manipulation of the reagent dispenser cap of FIG. 8.

FIGS. 8–10 show the reagent dispenser cap in an alternative preferred form, wherein the second reagent is provided in dry form impregnating a porous filter 54. More particularly, in this alternative, a modified squeeze bulb 30' defines a first chamber 49' for receiving a first reagent 48' in liquid form. This reagent chamber 49' is normally closed by a rupturable membrane ring 39' extending across a narrow neck 32', and an elongated nib 40' extends from the ring 39' into the reagent chamber. The porous filter 54 is installed within this neck region 32' and may be impregnated with a second reagent (not shown). The squeeze bulb 30' and narrowed neck 32' merge with a downwardly open sleeve 34' for slide-fit reception of the upper or proximal end of the tubular housing 12. FIG. 9 shows bendover displacement of the squeeze bulb 30' to bend the nib 40' sufficiently to sever the membrane ring 39' and thereby release the liquid reagent 48' for flow to the filter 54. FIG. 10 illustrates squeezing of the squeeze bulb 30' to deliver the liquid reagent 48' through the filter 54, with concurrent admixture with the second reagent carried by the filter, and for delivery of the mixed reagents to the specimen chamber 26, as previously described. Alternately, it will be understood that the second reagent and/or the filter 54 may be omitted in the case where a single liquid reagent is sufficient to meet the requirements of a particular test procedure.

The diagnostic strip assembly 18 is shown in one preferred form in FIGS. 2–4 and 11–12. As shown, the strip assembly 18 comprises a strip holder 56 mounted at the lower or distal end of the tubular housing 12, wherein the strip holder 56 includes an elongated support arm 58 having an elongated open channel 60 formed therein for receiving and supporting the elongated porous diagnostic strip 20. A lower end of the support arm 58 is joined to a generally disk-shaped mounting ring 62 carrying a cylindrical sleeve or fitment 64 sized for press-fit reception into the tubular housing 12. An outlet port 66 is formed in the mounting ring 62, at a lower end of the fitment 64, to permit controlled outflow of the specimen and mixed reagents, as will be described in more detail. As shown best in FIGS. 3 and 12, the fitment 64 defines a relatively shallow and narrow well 68 for receiving the swab tip 24 with collected specimen thereon, so that initial outflow of the mixed specimen and reagents constitutes a broth having a relatively concentrated level of specimen therein. The volume of liquid reagent or reagents delivered to the specimen chamber 26 is normally sufficient to immerse the swab tip 24 for thorough contact with the collected specimen.

The strip holder 56 carrying the diagnostic strip 20 is slidably carried within an outer protective sleeve 70, which can be formed conveniently and economically from transparent plastic. This protective sleeve 70 is shown with an open upper end 72 sized for slide-fit reception over the tubular housing 12, and an open lower end sized for slide-fit and substantially leak-free reception of the mounting ring 62 on the strip holder 56. Internal ribs 73 (FIG. 3) within the protective sleeve 70 define an internal track for slide-fit positioning of the diagnostic strip 20 substantially aligned with the transparent window 28 mounted on or otherwise formed integrally with the sleeve 70. From the mounting ring 62, the protective sleeve extends downwardly a sufficient distance for slide-fit and substantially leak-free reception of a generally cylindrical valve plug 76. This valve plug 76 facilitates controlled or regulated flow of the mixed specimen and reagents from the specimen chamber 26 to wet the lower end of the diagnostic strip 20.

More specifically, in the preferred form of the invention as shown in FIGS. 1–4 and 11–12, the valve plug 76 is rotatably carried within the lower end of the outer protective sleeve 70 and includes a valve pin 78 initially seated within and closing the outlet port 66 formed in the mounting ring 62 to prevent fluid outflow from the specimen chamber 26. As shown, this valve pin 78 is located off-axis relative to a centerline axis of rotation of the valve plug 76 within the outer sleeve 70, whereby such rotation is effective to displace the valve pin 78 away from the outlet port 66 and allow fluid outflow from the specimen chamber. In this condition, outflow of the mixed specimen and reagents is permitted across the top of the valve plug 76, through a transfer flow path or channel 80 formed between the top of the valve plug 76 and the underside of the mounting ring 62, for wetting the lower end of the diagnostic strip 20.

In a preferred construction, a transfer wick 82 in the form of a porous sponge block of the like may be placed into the transfer channel 80 to facilitate fluid flow from the specimen chamber 26 to the diagnostic strip 20. FIGS. 2–3 and 11–12 show this transfer wick 82 constrained between a pair of upstanding side rails 84 at the top of the valve plug 76. When the valve plug 76 is in its initial rotational position with the valve pin 78 closing the outlet port 66, the transfer wick 82 is retained out of alignment with the outlet port. However, when the valve plug 76 is rotated through a sufficient angle, such as about 90 degrees, the transfer wick 82 is rotated for direct contact alignment between the outlet port 66 at one end, and the lower end of the diagnostic strip 20 at the other. In this regard, limited rotation of the valve plug 76 can be accommodated by providing a short lug 86 on the top of the plug, wherein the lug 86 is circumferentially disposed within an arcuate notch 88 formed in the periphery of the mounting ring 62. For optimum results, the transfer wick 82 is normally constrained under compression, so that an upstream end thereof subsequently aligned with the outlet port 66 will expand through the port as viewed in FIG. 12 for direct or near-direct contact with the swab tip 24, thereby insuring that the initial fluid flow through the transfer wick to the strip 20 is heavily concentrated with the collected specimen.

Moreover, if desired, the transfer wick 82 may be impregnated with one or more additional reagents for contacting the specimen upon transfer flow therethrough. Alternately, if desired, the valving function provided by rotating the valve plug 76 may be substituted by coating or impregnating the transfer wick 82 with a time release material adapted for controlled time dissolution in the presence of the mixed specimen and reagents for controlled time transfer of the fluid to the strip 20.

Accordingly, rotation of the valve plug 76 permits the mixed specimen and reagents to flow from the specimen chamber 26 and through the transfer wick 82 to the lower end of the diagnostic strip 20. From here, the fluid flows upwardly through the diagnostic strip 20 by wick action. Such wick flow may be insured or enhanced by venting the upper end of the outer protective sleeve 70, by means of a small vent notch 90 shown in FIG. 2. The inclusion of one or more additional reagents in dry form along the length of the strip 20 enables further reactions with the specimen to produce a visible test result such as a color change reflecting the presence or nonpresence of certain target organisms. Appropriate labels (not shown) may be applied to the exterior of the sleeve 70, in suitable juxtaposition to the window 28, to facilitate and explain accurate reading of the test result. Moreover, visual observation of the test result is desirably enhanced by forming the window 28 for magnification of the underlying diagnostic strip 20.

As one example of use of the diagnostic test unit 10, the device may be employed to perform a strep extraction test. In such test, a patient cell specimen is collected in a normal manner by use of the swab 14, to collect cells from the throat of a patient on the fibrous swab tip 24. The swab 14 is then placed immediately and directly into the tubular housing 12, with the swab tip 24 seated within the fitment well 687 and the proximal end of the housing is closed by the reagent dispenser cap 16. The dispenser cap 16 may contain a first reagent such as citric or acetic acid within the squeeze bulb chamber 48, and a second reagent such as sodium nitrite or a similar nitrite compound within the second chamber 50. The dispenser cap 16 is manipulated as described above to mix these two reagents and to dispense them to the specimen chamber 26 for contacting the collected specimen. The reagent solution is allowed to digest the specimen sample for a defined holding period, typically about 60–90 seconds, after which the valve plug 76 is rotated to permit fluid transfer flow from the specimen chamber 26 to the diagnostic strip 20. The strip 20 comprises a porous paper-based element impregnated at predetermined points with additional agents such as a neutralizing buffer such as trishydroxy-methylaminomethane (TRIS), for reacting with the treated specimen to yield a first color change indicating the presence of strep organism, or a second color change indicating the absence of strep organism. As previously described, the initial fluid flow to the strip 20 contains a high concentration of the target specimen for achieving fast, strong, and highly reliable test results, with sufficient excess liquid reagent being normally provided to insure driving the test to a conclusion. Following visual reading of the test, the entire test unit may be discarded in an appropriate manner.

FIG. 13 shows an alternative preferred form of the invention wherein a modified valve plug 176 is provided for use in the diagnostic test unit 10, constructed otherwise as previously shown and described, and with functional counterpart components being referred to by common reference numerals increased by 100. As shown in FIG. 13, the modified valve plug 176 supports a modified transfer wick 182 having a relatively broad upstream end for rotary movement into alignment with the specimen chamber 26 via the outlet port 66 (not shown in FIG. 13), and a downstream end defining multiple fingers 176' and 176" for contacting the lower end of the diagnostic strip 20. In this version, the fingers 176' and 176" may carry or be impregnated with different selected reagents, and the valve plug can be rotated in step or increments so that the specimen flowing to the strip is first contacted by one reagent and then by another reagent.

FIG. 14 illustrates another alternative form of the invention, wherein a modified strip holder 156 is provided for use in the diagnostic test unit 10, which is again otherwise constructed in the manner previously shown and described, and whose functionally analogous structures are again identified by common reference numbers increased by 100. In this embodiment, the strip holder 156 includes a modified support arm 158 formed to include multiple channels 160 for respectively receiving and supporting a plurality of diagnostic strips 20. Each of the diagnostic strips 20 may be impregnated with different agents aimed at interacting with the specimen to perform different assays in parallel. Such multiple tests may be performed at the same time upon appropriate transfer of the fluid from the specimen chamber 26 (not shown in FIG. 14) to the lower ends of the strips 20.

FIGS. 15 and 16 show a further alternative preferred form of the invention, wherein the housing and cap components of the test unit are constructed predominantly from blow molded components which can be manufactured quickly and economically, with functionally related structures referred to by common reference numerals increased by 200. More specifically, as shown in FIG. 15, a unitary blow molded blank 200 is formed to include an upper segment 202 defining a squeeze bulb 230 with a related narrowed neck 232 joined to a downwardly extending sleeve 234, for use in constructing a reagent dispenser cap for the test unit. This upper segment of the blow molded blank merges through a transition segment 204 of reducing or stepped down diametric size, with a lower housing segment 206. This lower housing segment 206 defines a tubular housing 212 forming the specimen chamber 26, with a lower end of the specimen chamber 26 terminating generally at an outlet port 266 defined by a region of reduced cross sectional size. Below the outlet port 266, a transfer channel 280 leads to a blow port 208 at a lower end of the blank. Importantly, a lower end of the transfer channel 280 communicates with an upwardly extending strip channel 260 formed alongside the transfer chamber 280 and the specimen chamber 26, separated therefrom by an internal stand-off or wall 209.

The above described blow molded blank is quickly and easily modified to produce the diagnostic test unit of the present invention, as viewed in fully assembled form in FIG. 16. More specifically, as shown in FIG. 15, the blank is cross cut as indicated at 211 near the lower end of the upper sleeve 234, and again at an angular cut as indicated at 213 near the upper end of the tubular housing 212. These cuts 211, 213 permit separation of the blank components for installation of a nib unit 236 into the upper segment 202 to form a reagent dispenser cap 216, and to permit installation of a transfer filter or wick 282 generally at the outlet port 266 of the lower segment 206. A diagnostic strip 20 is fitted through the blow port 208 into the strip channel 260, and the blow port 208 is appropriately closed and sealed. A swab 14 can then be placed into the specimen chamber 26, and the reagent dispenser cap 216 fitted onto the upper end of the tubular housing 212 to close the test unit.

In use, the test unit embodiment of FIG. 16 operates generally in the same manner as previously described with respect to FIGS. 1–14. More particularly, the swab 14 is utilized to collect a target specimen and is then placed into the specimen chamber 26. The dispenser cap 216 is fitted onto the housing 212 and manipulated to release the one or more reagents therein for delivery to the specimen. The transfer filter 282 may be impregnated with additional reagents and/or a time release coating to regulate fluid flow from the specimen chamber 26 to the lower end of the diagnostic strip 20 via the transfer chamber 280. The fluid will wet the lower end of the strip 20 and thus flow along the strip by wick action. Appropriate reagents are incorporated along the strip length to react with the test constituents in a manner yielding a visual test result which can be observed from the exterior of the test unit by forming the blow molded components from a sufficiently transparent plastic material.

The improved diagnostic test unit of the present invention thus provides a simple and easy to use apparatus for performing one or more diagnostic assays in a substantially self contained compact package. Personnel exposure to the collected specimen is limited to standard specimen collection with a swab or the like, wherein the specimen may be placed directly and enclosed immediately within the test unit where further personnel contact is substantially precluded. With the specimen placed into the test unit, the selected test procedure can be performed quickly and easily, and in a manner permitting requisite delay or incubation periods as may be appropriate to a particular test. The delivery of the specimen to the diagnostic strip for reading proceeds with an initial concentrated specimen sample to achieve a rapid and accurate test read-out, while additionally providing sufficient excess fluid to insure that the test is driven to a conclusion. Moreover, the test unit components insure that the assay proceeds in the correct sequence and timing and with the flow of fluid to the strip 20 sufficiently regulated to a rate which the strip can accommodate by wick action. The geometry of the test unit, with the elongated diagnostic strip mounted to extend back alongside the specimen chamber within the tubular housing, provides a relatively compact overall package. At the conclusion of a test, the test unit can be economically and easily discarded in accordance with normal disposal practices.

A variety of further modifications and improvements in and to the diagnostic test unit of the present invention will be apparent to those skilled in the art. Accordingly, no limitation on the invention is intended by way of the foregoing description and accompanying drawings, except as set forth in the appended claims.

What is claimed is:

1. A diagnostic test unit, comprising:
    an elongated hollow housing having a proximal end and a distal end, said housing defining a specimen chamber for receiving therein a specimen for analysis;
    a cap removably mounted on said proximal end of said housing; and
    a diagnostic strip assembly mounted on said distal end of said housing, said diagnostic strip assembly including a diagnostic strip of a porous material for fluid flow along said strip by wick action, means for supporting said diagnostic strip to extend generally along the exterior of said specimen chamber, and transfer means for controllably coupling a specimen within said specimen chamber for flow to and contact with one end of said diagnostic strip, whereby the specimen will flow along said strip by wick action;
    said strip carrying at least one reagent for contact by the specimen flowing along said strip to provide a visual indication of test result.

2. The diagnostic test unit of claim 1 wherein said housing comprises a tubular housing.

3. The diagnostic test unit of claim 1 further including means for collecting a specimen, said collecting means having a size and shape to fit into said specimen chamber.

4. The diagnostic test unit of claim 3 wherein said collecting means comprises a swab.

5. The diagnostic test unit of claim 4 wherein said diagnostic strip assembly comprises a generally cylindrical fitment positioned within said housing at the distal end thereof, and an outlet port for outflow of the specimen from said specimen chamber to said strip, said fitment defining a well for relatively close fit reception of a tip of said swab.

6. The diagnostic test unit of 1 wherein said means for supporting said diagnostic strip comprises a protective outer sleeve mounted about said housing and having said strip supported therein between said housing and said sleeve, said sleeve including a transparent window to permit visual observation of said strip.

7. The diagnostic test unit of claim 6 wherein said window comprises a magnification window.

8. The diagnostic test unit of claim 1 wherein said transfer means comprises valve means for normally closing an outlet port disposed between said specimen chamber and said one end of said strip, said valve means being movable from a normally closed position to an open position permitting the specimen to flow from said specimen chamber to said one end of said strip.

9. The diagnostic test unit of claim 8 wherein said valve means comprises a valve plug rotatably between said closed and open positions.

10. The diagnostic test unit of claim 8 further including a transfer wick extending from said outlet port to said one end of said strip.

11. The diagnostic test unit of claim 10 wherein said transfer wick comprises a porous compressible element retained under compression between said outlet port and said strip, a portion of said compressible element being adapted for expansion through said outlet port to extend partially into said specimen chamber upon movement of said valve means to said open position.

12. The diagnostic test unit of claim 10 wherein said transfer wick is impregnated with at least one additional reagent.

13. The diagnostic test unit of claim 10 wherein said transfer wick includes an upstream end for alignment with said outlet port, and a downstream end defined by multiple fingers each carrying a different reagent and adapted for respective contact with said one end of said strip in response to stepwise movement of said valve means.

14. The diagnostic test unit of claim 1 wherein said transfer means comprises a transfer wick interposed between said specimen chamber and said one end of said strip.

15. The diagnostic test unit of claim 14 wherein said transfer wick includes a time delay coating adapted for controlled dissolution upon contact with mixed specimen and reagent within said specimen chamber.

16. The diagnostic test unit of claim 1 wherein said cap comprises a reagent dispenser cap including means for delivering at least one reagent into said specimen chamber for contacting a specimen therein.

17. The diagnostic test unit of claim 1 wherein said diagnostic stip assembly includes a plurality of diagnostic strips, said transfer means controllably coupling a specimen within said specimen chamber for flow to and contact with one end of each of said strips.

18. A diagnostic test unit, comprising:
an elongated hollow housing having a proximal end and a distal end, said housing defining a specimen chamber for receiving therein a specimen for analysis;
a reagent dispenser cap removably mounted on said proximal end of said housing, said reagent dispenser cap including means for delivering at least one reagent into said specimen chamber for contacting a specimen therein; and
a diagnostic strip assembly mounted on said distal end of said housing, said diagnostic strip assembly comprising a diagnostic strip or a porous material for fluid flow along said strip by wick action, a strip holder having a channel therein for receiving and supporting said strip, mounting means for supporting said strip holder on the exterior of said housing generally at the distal end of said housing, a protective outer sleeve mounted about said strip holder and said strip generally at the distal end of said housing, said sleeve having a transparent window to permit visual observation of said strip, and transfer means between said distal end of said housing and one end of said strip for controllably coupling mixed specimen and reagent within said specimen chamber for flow to and contact with one end of said strip, whereby mixed specimen and reagent will flow along said strip by wick action;
said strip carrying at least one reagent for contact by mixed specimen and reagent flowing along said strip to provide a visual indication of test result.

19. The diagnostic test unit of claim 18 wherein said housing comprises a tubular housing.

20. The diagnostic test unit of claim 18 further including means for collecting a specimen, said collecting means having a size and shape to fit into said specimen chamber.

21. The diagnostic test unit of claim 20 wherein said collecting means comprises a swab.

22. The diagnostic test unit of claim 21 wherein said diagnostic strip assembly comprises a generally cylindrical fitment positioned within said housing at the distal end thereof, and an outlet port for outflow of mixed specimen and reagent from said specimen chamber to said strip, said fitment defining a well for relatively close fit reception of a tip of said swab.

23. The diagnostic test unit of claim 18 wherein said transfer means comprises valve means for normally closing an outlet port disposed between said specimen chamber and said one end of said strip, said valve means being movable from a normally closed position to an open position permitting mixed specimen and reagent to flow from said specimen chamber to said one end of said strip.

24. The diagnostic test unit of claim 23 wherein said valve means comprises a valve plug rotatably carried by said sleeve.

25. The diagnostic test unit of claim 23 further including a transfer wick extending from said outlet port to said one end of said strip.

26. The diagnostic test unit of claim 25 wherein said transfer wick comprises a porous compressible element retained under compression between said outlet port and said strip, a portion of said compressible element being adapted for expansion through said outlet port to extend partially into said specimen chamber upon movement of said valve means to said open position.

27. The diagnostic test unit of claim 25 wherein said transfer wick is impregnated with at least one additional reagent.

28. The diagnostic test unit of claim 18 wherein said transfer means comprises a transfer wick interposed between said specimen chamber and said one end of said strip.

29. The diagnostic test unit of claim 28 wherein said transfer wick includes a time delay coating adapted for controlled dissolution upon contact with mixed specimen and reagent within said specimen chamber.

30. The diagnostic test unit of claim 18 wherein said window comprises a magnification window.

* * * * *